US00PP16954P2

(12) United States Plant Patent

Parthasarathy et al.

(10) Patent No.: US PP16,954 P2

(45) Date of Patent: Aug. 8, 2006

(54) *CORDYLINE* PLANT NAMED 'MAROON MAGIC'

(50) Latin Name: *Cordyline terminalis*
Varietal Denomination: Maroon Magic

(76) Inventors: Gopalaswamy Parthasarathy, "Srinivasa", 237/46, Fifth Main Road, Chamrajpet, Bangalore 560018 (IN); Parthasarathy Mukundan, "Srinivasa", 237/46, Fifth Main Road, Chamrajpet, Bangalore 560018 (IN)

( * ) Notice: Subject to any disclaimer, the term of this patent is extended or adjusted under 35 U.S.C. 154(b) by 0 days.

(21) Appl. No.: 11/141,584

(22) Filed: May 31, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Cordyline* plant named 'Maroon Magic', characterized by its upright, uniform and vigorous growth habit; slender stems with short internodes; dense and bushy growth habit; long arching linear leaves that are glossy and uniformly dark burgundy to brown in color with dark purple-colored margins; and excellent keeping quality.

1 Drawing Sheet

Botanical designation: *Cordyline terminalis.*
Cultivar denomination: 'Maroon Magic'.

BACKGROUND OF THE INVENTION

The present invention relates to a new and distinct cultivar of *Cordyline* plant, botanically known as *Cordyline terminalis,* and hereinafter referred to by the cultivar name Maroon Magic.

The new *Cordyline* is the result of a planned breeding program conducted by the Inventors in Charmarajpet, Bangalore, India. The objective of the breeding program is to create new vigorous *Cordyline* cultivars with dense and bushy plant habit, unique leaf coloration, interesting leaf shapes, resistance to pathogens and pests common to *Cordylines* and tolerance to low temperatures.

The new *Cordyline* originated from a cross-pollination made by the Inventors on Jan. 12, 1995 of the *Cordyline terminalis* cultivar Mahatma, not patented, as the female, or seed, parent with the *Cordyline terminalis* cultivar Mahadevi, not patented, as the male, or pollen, parent. The new *Cordyline* was discovered and selected by the Inventors in 1995 as a single plant within the progeny of the stated cross-pollination in a controlled environment in Chamarajpet, Bangalore, India. The new *Cordyline* was selected on the basis of its plant habit, leaf shape and uniquely colored foliage.

Asexual propagation of the new cultivar by cuttings at Chamarajpet, Bangalore, India since July, 1996, has shown that the unique features of this new *Cordyline* plant are stable and reproduced true to type in successive generations of asexual propagation.

SUMMARY OF THE INVENTION

The new *Cordyline* has not been observed under all possible environmental conditions. The phenotype may vary somewhat with variations in environment such as temperature and light intensity, without, however, any variance in genotype. The following traits have been repeatedly observed and are determined to be the unique characteristics of 'Maroon Magic'. These characteristics in combination distinguish 'Maroon Magic' as a new and distinct cultivar:

1. Upright, uniform and vigorous growth habit.
2. Slender stems with short internodes; dense and bushy growth habit.
3. Long arching linear leaves that are glossy and uniformly dark burgundy to brown in color with dark purple-colored margins.
4. Excellent keeping quality.

Plants of the new *Cordyline* can be compared to plants of the female parent, the cultivar Mahatma. In side-by-side comparisons conducted in Chamarajpet, Bangalore, India, plants of the new *Cordyline* differed from plants of the cultivar Mahatma in the following characteristics:

1. Plants of the new *Cordyline* were more vigorous, denser and bushier than plants of the cultivar Mahatma.
2. Plants of the new *Cordyline* had narrower leaves than plants of the cultivar Mahatma.
3. Leaf color of plants of the new *Cordyline* was more uniform than leaf color of plants of the cultivar Mahatma.
4. Plants of the new *Cordyline* and the cultivar Mahatma differed in leaf coloration.

Plants of the new *Cordyline* can be compared to plants of the male parent, the cultivar Mahadevi. In side-by-side comparisons conducted in Chamarajpet, Bangalore, India, plants of the new *Cordyline* differed from plants of the cultivar Mahadevi in the following characteristics:

1. Plants of the new *Cordyline* were more vigorous, faster-growing, denser and bushier than plants of the cultivar Mahadevi.
2. Plants of the new *Cordyline* had narrower and longer leaves than plants of the cultivar Mahadevi.
3. Leaf color of plants of the new *Cordyline* was more uniform than leaf color of plants of the cultivar Mahadevi.
4. Plants of the new *Cordyline* and the cultivar Mahadevi differed in leaf coloration.

Plants of the new *Cordyline* can also be compared to plants of the cultivar Big Doll, not patented. In side-by-side comparisons conducted in Charmarajpet, Bangalore, India, plants of the new *Cordyline* differed from plants of the cultivar Big Doll in the following characteristics:

1. Plants of the new *Cordyline* were more vigorous, denser and bushier than plants of the cultivar Big Doll.
2. Plants of the new *Cordyline* had narrower and longer leaves than plants of the cultivar Big Doll.
3. Leaf color of plants of the new *Cordyline* was more uniform than leaf color of plants of the cultivar Big Doll.
4. Plants of the new *Cordyline* and the cultivar Big Doll differed in leaf coloration.

Plants of the new *Cordyline* can also be compared to plants of the cultivar Tricolor, not patented. In side-by-side comparisons conducted in Chamarajpet, Bangalore, India, plants of the new *Cordyline* differed from plants of the cultivar Tricolor in the following characteristics:

1. Plants of the new *Cordyline* denser and bushier than plants of the cultivar Tricolor.
2. Plants of the new *Cordyline* had narrower and longer leaves than plants of the cultivar Tricolor.
3. Leaf color of plants of the new *Cordyline* was more uniform than leaf color of plants of the cultivar Tricolor.
4. Plants of the new *Cordyline* and the cultivar Tricolor differed in leaf coloration.

DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Cordyline*. The photograph comprises a side perspective view of typical plants of 'Maroon Magic' grown in a container.

DETAILED BOTANICAL DESCRIPTION

The aforementioned photographs and following observations and measurements describe plants of the new *Cordyline* that were grown in 25-cm containers, in Homestead, Fla., in a polypropylene-covered shadehouse with light levels about 2,500 foot-candles. During the production of the plants, day temperatures ranged from 5 to 40° C. and night temperatures ranged from 5 to 30° C. Plants used for the photographs and description were about two years from planting. Color references are made to The Royal Horticultural Society Colour Chart, 1995 Edition, except where general terms of ordinary dictionary significance are used.

Botanical classification: *Cordyline terminalis* cultivar Maroon Magic.

Parentage:

*Female, or seed, parent.*—*Cordyline terminalis* cultivar Mahatma, not patented.

*Male, or pollen, parent.*—*Cordyline terminalis* cultivar Mahadevi, not patented.

Propagation:

*Method.*—By cuttings.

*Time to initiate roots.*—Summer: About 15 to 18 days at 25 to 38° C. Winter: About 25 to 30 days at 18 to 25° C.

*Time to produce a rooted young plant.*—About one to two months.

*Root description.*—Fine, fibrous, fleshy; white in color.

*Rooting habit.*—Freely branching; vigorous; dense and profuse.

Plant description:

*Plant shape.*—Upright plant habit. Short internodes; dense and bushy growth habit.

*Plant height.*—About 71 cm.

*Plant diameter or spread.*—About 66 cm.

*Plant vigor.*—Vigorous.

*Growth rate.*—Relatively fast.

*Stem description.*—Diameter, at base: About 1.3 cm; slender. Internode length: About 5 mm. Color, young: Close to 187A. Color, mature: 146A overlain with close to 199D. Texture, young: Smooth, glabrous. Texture, mature: Glabrous; woody.

*Foliage description.*—Orientation: Initially erect to outwardly arching. Arrangement: Whorled. Shape: Linear. Apex: Sharply acute. Margin: Entire. Texture, upper and lower surfaces: Leathery; smooth, glabrous. Luster, upper surface: Glossy. Luster, lower surface: Dull. Venation pattern: Parallel. Length: About 41 cm. Width, at broadest point: About 4.8 cm. Color: Developing leaves, upper surface: Darker green than 147A overlain with 187A; narrow margin, close to 187A. Developing leaves, lower surface: Between 187A and 202A underlain with darker green than 147A. Fully expanded leaves, upper surface: Between 187A and 202A; narrow margin, close to 187B to 187C. Fully expanded leaves, lower surface: Between 187A and 202A underlain with darker green than 147A. Venation, upper and lower surfaces: Close to 187A. Petiole: Length: About 12 cm. Diameter, at base: About 1.1 cm. Texture, upper and lower surface: Smooth, glabrous. Color, upper surface: Towards the leaf, 187A to 187C; towards the stem, close to 193B. Color, lower surface: Towards the leaf, close to 187A; towards the stem, close to 202A.

Flower description: Flowers have not been observed on plants of the new *Cordyline*.

Keeping quality: Plants of the new *Cordyline* are durable and will maintain good leaf substance indefinitely under interior conditions.

Disease/pest resistance: Under commercial conditions, resistance to pathogens to pests common to *Cordylines* has not been observed.

Temperature tolerance: Plants of the new *Cordyline* have been observed to tolerate temperatures from 5 to 45° C.

It is claimed:

1. A new and distinct cultivar of *Cordyline* plant named 'Maroon Magic' as illustrated and described.

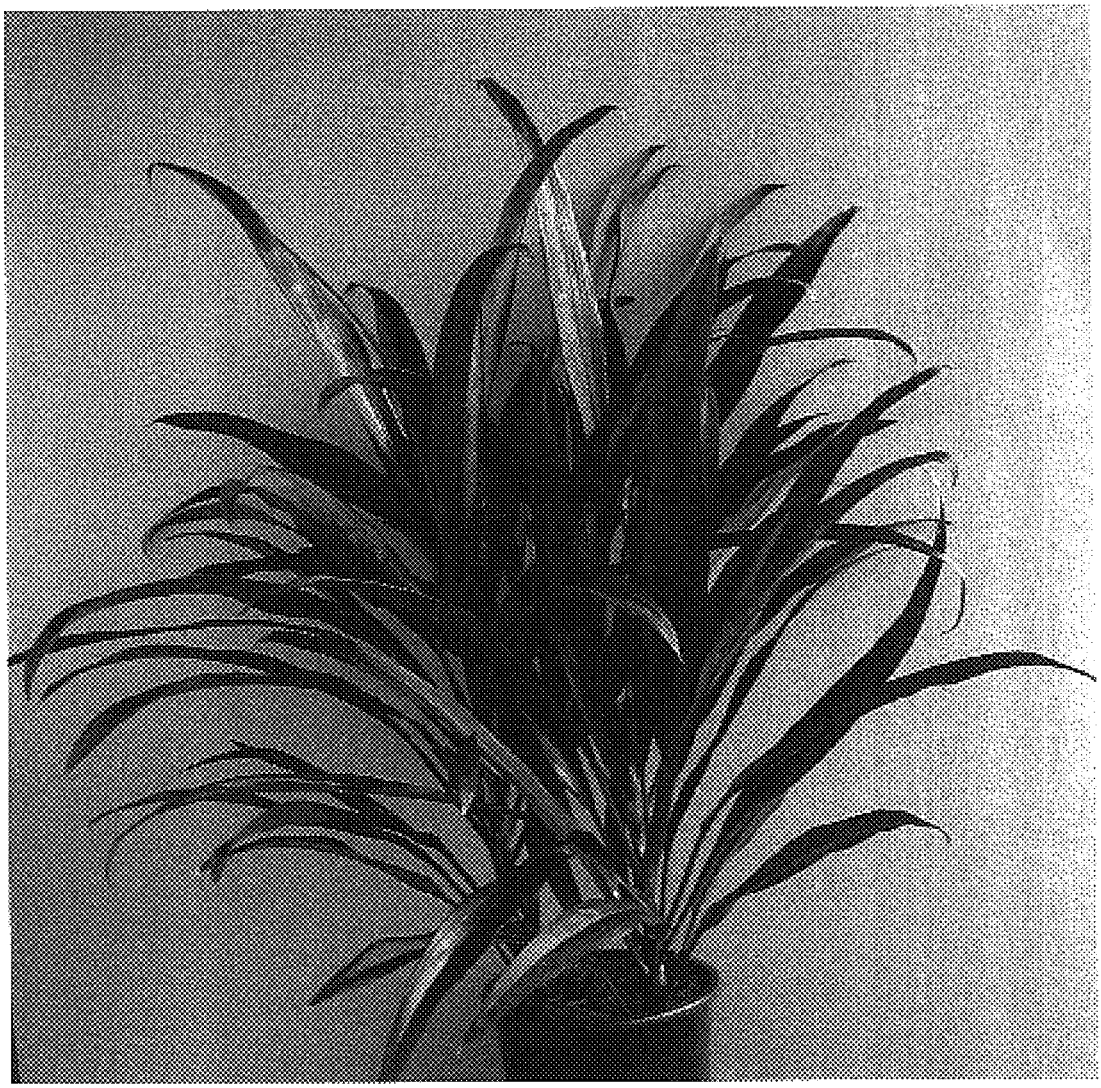

* * * * *